United States Patent [19]

Tessmann et al.

[11] Patent Number: 5,167,614
[45] Date of Patent: Dec. 1, 1992

[54] PROSTATIC STENT

[75] Inventors: Terri L. Tessmann, Racine, Wis.; Jay R. Goldberg, Libertyville; John A. Shimkus, Frankfort, both of Ill.; Gerald T. Friso, Racine, Wis.

[73] Assignee: Medical Engineering Corporation, Racine, Wis.

[21] Appl. No.: 784,293

[22] Filed: Oct. 29, 1991

[51] Int. Cl.$^5$ .............................................. A61M 5/00
[52] U.S. Cl. ............................................ 604/8; 623/1
[58] Field of Search ................................ 623/1; 604/8

[56]     References Cited
     U.S. PATENT DOCUMENTS

| | | | |
|---|---|---|---|
| 4,382,445 | 5/1983 | Sommers | 604/8 |
| 4,596,577 | 6/1986 | Sato | 623/1 |
| 4,710,181 | 12/1987 | Fuqua | 604/280 |
| 4,732,152 | 3/1988 | Wallstein et al. | 623/1 |
| 4,737,147 | 4/1988 | Ferrando et al. | 604/96 |
| 4,738,666 | 4/1988 | Fuqua | 604/280 |
| 4,740,207 | 4/1988 | Kreamer | 623/1 |
| 4,830,003 | 5/1989 | Wolff et al. | 128/343 |
| 4,877,030 | 10/1989 | Beck et al. | 623/1 |
| 4,950,227 | 8/1991 | Savin et al. | 623/1 |
| 4,955,859 | 9/1990 | Zilber | 604/8 |

OTHER PUBLICATIONS

Nissenkorn, "Urologists At Work," article, Experience with a New Self-Retaining Intraurethral Catheter in Patients with Urinary Retention: A Preliminary Report, *The Journal of Urology*, vol. 142, p. 92 (1989).

Pharmaplast "Prostacath" drawing, undated.

*Primary Examiner*—David Isabella
*Assistant Examiner*—Gina M. Gualtieri

[57]     ABSTRACT

A stent for maintaining fluid flow through a body passage in a patient comprises a tubular member having an inlet at one end, an outlet at the other end and a lumen extending from the inlet to the outlet. The preferred stent also includes at least one projection on the outer wall of the tubular member which enters the wall of the body passage when the stent is rotated in the proper direction. A kit also is disclosed which includes the stent and a tool for grasping and turning the stent from outside the patient's body.

2 Claims, 2 Drawing Sheets

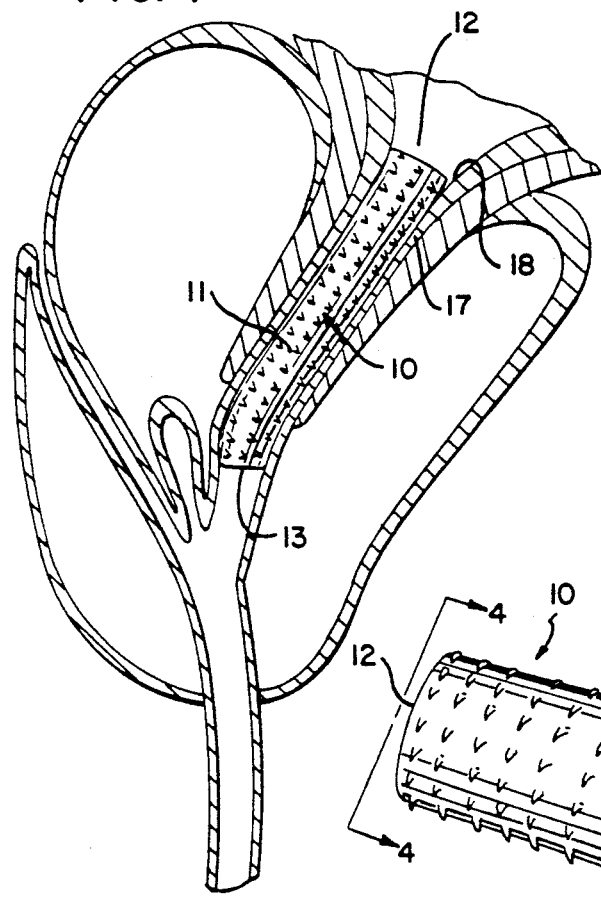
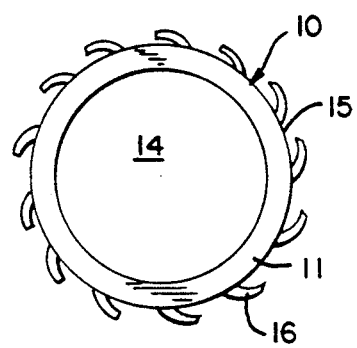
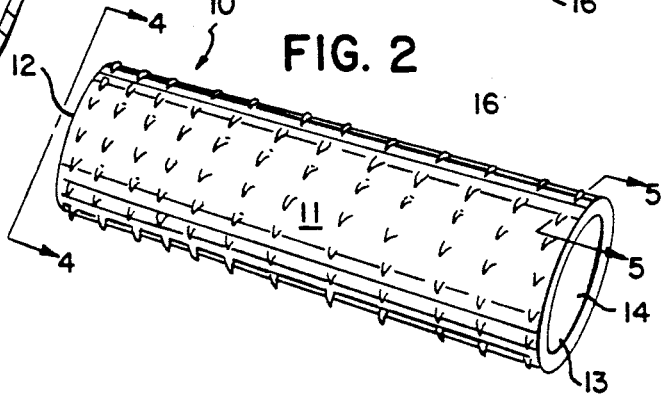
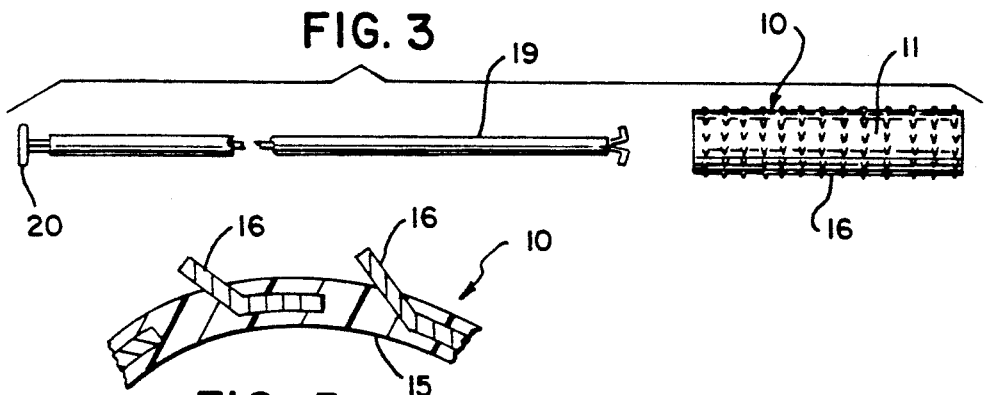
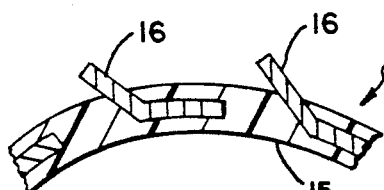

PROSTATIC STENT

FIELD OF THE INVENTION

The present application relates generally to stents for maintaining flow through a body passage. More particularly, it relates to prostatic stents which are used to remedy or prevent bladder outlet obstructions in humans.

BACKGROUND OF THE INVENTION

The use of stents to maintain fluid flow in body passages is well known. In addition, it is known to use stents to maintain urine flow through the prostatic urethra. In U.S. Pat. No. 4,955,859, a prostatic stent is disclosed which includes means for frictionally engaging the urethra walls to prevent the device from migrating back into the bladder or down into the urethra.

It would be advantageous to have a stent that could both provide and maintain flow through a body passage, such as the urethra, which had a more reliable means than just frictional contact to prevent migration of the stent from the body passage.

SUMMARY OF THE INVENTION

It is an object of the present invention to disclose a stent which both provides and maintains flow through a body passage and which has means for anchoring the stent in the wall of the body passage.

The stent of the present invention comprises an elongated tubular member having an inlet at one end, an outlet at the other end, a lumen connecting the inlet to the outlet so that fluid can flow through the stent and anchoring means which anchor the stent in the wall of a body passage to prevent any migration and which can be manipulated manually from outside the body to anchor the stent and to remove the stent from its anchored position when it is no longer needed.

In one embodiment, the anchoring means includes a plurality of sharp unidirectional, hook-like projections on the outer wall of the tubular member. The tubular member can be grasped from outside the body with an elongated grasping tool and manually turned with the tool in one direction to anchor the stent to the wall of the body passage and turned in the opposite direction to remove the stent from the anchored position so it can be removed from the body passage.

In another embodiment, the tubular member is a relatively rigid sheet which is coiled concentrically. The sheet has an outer lateral edge which is provided with teeth that can anchor the stent to the wall of the body passage. The coiled sheet can be grasped and turned in one direction with a grasping tool so that the coil expands and the teeth positively anchor the stent to the wall of the passage. The stent can be removed when it is no longer needed by grasping the stent again with the tool and turning the stent in the opposite direction to disengage the teeth and to more tightly coil the sheet.

In a further embodiment, the stent may be a tubular member having one or more relatively large projections that will anchor the stent to the passage wall so that when the stent is grasped from the outside with a tool and turned in one direction the projection(s) will engage the body passage wall. The stent can be removed by disengaging the projections by grasping the stent with a tool and turning in the opposite direction. The stent may be provided in a kit which also contains a suitable grasping tool.

It will be apparent to those skilled in the art that the foregoing objects and further advantages can be obtained by the practice of the present invention.

BRIEF DESCRIPTION OF THE DRAWINGS

In the drawings:

FIG. 1 is a schematic view of one embodiment of a stent of the present invention positioned within a prostatic urethra;

FIG. 2 is an enlarged perspective view of the stent of FIG. 1;

FIG. 3 is a view of the stent of FIG. 1 and a suitable grasping tool;

FIG. 4 is a sectional view of the stent taken along the lines 4—4 in FIG. 2;

FIG. 5 is an enlarged view taken along lines 5—5 in FIG. 2;

DESCRIPTION OF THE PREFERRED EMBODIMENT

Figure 6:
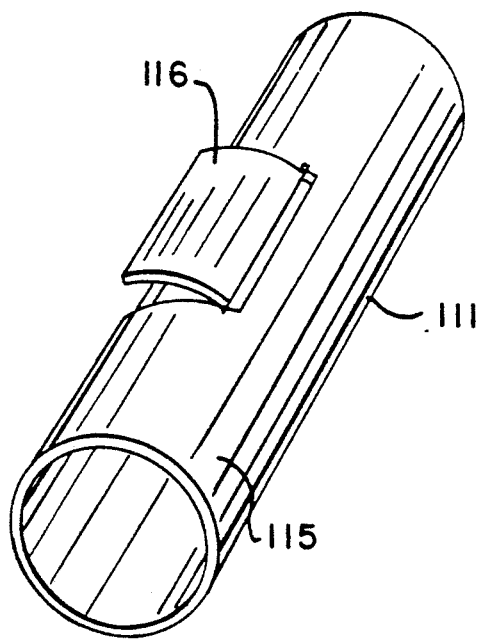
FIG. 6 is a perspective view of another embodiment of the stent.

As seen in FIGS. 1 to 5, the stent 10 of the present invention comprises an elongated tube 11 of a biocompatible material, e.g. a metal tube covered with a medical grade silicone rubber. The tube 11 has in inlet 12 at one end, an outlet 13 at the other end and a lumen 14 which extends from the inlet 12 to the outlet 13. As seen best in FIGS. 4 and 5, the outer wall 15 of the tube 11 has a plurality of unbarbed, unidirectional, hook-like projections 16 which can be physically anchored in the wall 17 of the urethra 18. If desired, the outer wall 15 of the tube and the projections 16 can be covered by a layer of lubricious hydrophilic material (not shown) which facilitates the introduction of the stent into the urethra and prevents the projections from causing any damage until the layer is washed away.

In the embodiment seen in FIG. 6, the tube 111 has a single, large projection 116 on the outer wall 115.

Figure 7:
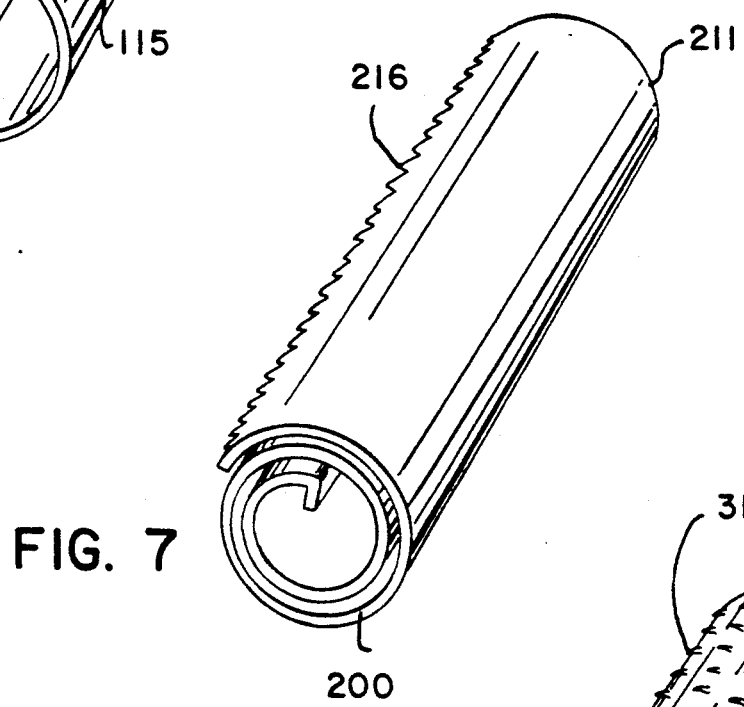
FIG. 7 is a perspective view like FIG. 6 of still another embodiment of the stent.
Figure 8:
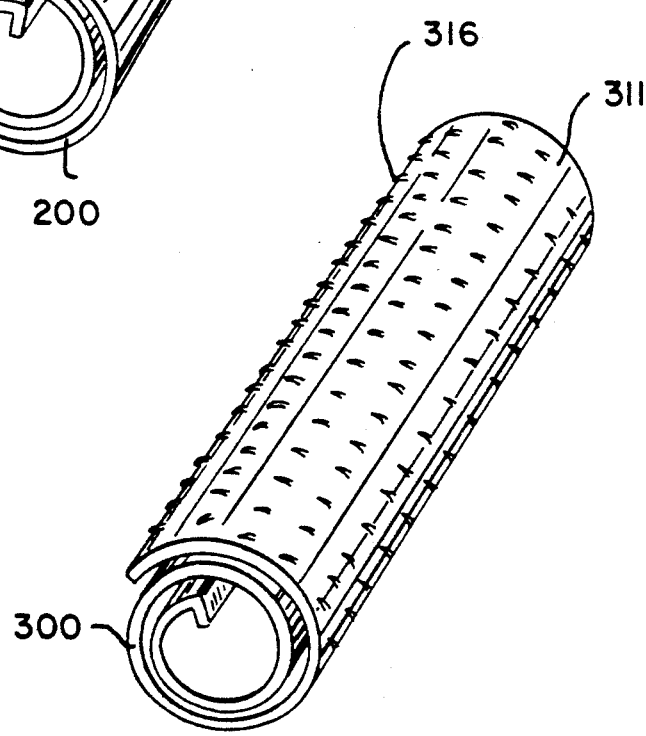
FIG. 8 is a perspective view like FIG. 6 of a further embodiment of the stent.

In the stents of FIGS. 7 and 8, the tube 211 is formed of a coiled sheet 200 of a relatively rigid material which has a memory which causes it to expand outwardly when heated, such as Nitinol, or when it is unrestrained. The coiled sheet 200 can be restrained, such as by a sleeve or by a tie, until it is positioned in place. When it is no longer restrained the coiled sheet 200 because of its memory expands outwardly until it contacts the wall of the body passage. The relatively sharp teeth 216 outer edge of the coiled sheet serve as a projection to anchor the stent. The embodiment of FIG. 8, is like that of FIG. 7, except that the coiled sheet 300 includes projections 316 on the outer wall to assist in anchoring.

The stent of the present invention obviously may take other forms than those described; however, in any case the tube whether cylindrical o coiled should be capable of maintaining a usable lumen for the passage of fluid even when pressed upon by expanding body tissue.

In the preferred method of use of the stents of FIGS. 1–5 and FIG. 6, the inlet end of the stent is introduced into a body passage and moved to the desired location by advancing the stent and turning it clockwise with a grasping tool 19 (seen only in FIG. 3). When the stent 10 is properly positioned, the handle end 20 of the grasping tool 19 which extends outside the body of the patient is turned counterclockwise to anchor the projection(s) in the wall of the body passage. When the stent is no longer needed, it is removed from the body passage by grasping the outlet end with the grasping tool and simultaneously withdrawing the stent while turning the handle clockwise to disengage the projections.

In the preferred method of use for the stents of embodiments of FIGS. 7 and 8 in which the coiled sheet forms the tube, the coiled sheet is introduced into the body passage and moved in the desired position, preferably by use of the grasping tool 19. The restraints, if any, are then removed whereupon the coiled sheet expands because of its memory to a larger diameter which fills the lumen of the body passage. The stent can then be turned counterclockwise by use of the grasping tool so that the outer edge is anchored in the wall of the body passage. The stent may be removed by grasping the inner end with the grasping tool 19 and turning clockwise to tighten the coiled sheet to make it smaller in diameter and to disengage the anchored teeth while simultaneously withdrawing the tool and stent.

It will be readily apparent to those skilled in the art that a variety of changes and modifications can be made without departing from the spirit and scope of the invention. For example, in place of the restraining sleeve the coiled sheet tube can be restrained by tying it in that condition with a material that is quickly dissolved by body fluids and/or bioabsorbed or a material that can be severed with the grasping tool when the stent is properly in place. Therefore, the invention is not to be limited except by the claims which follow.

We claim:

1. A stent for maintaining fluid flow through the urethra which has a wall, said stent comprising:
   a. an elongated tube having an inlet at one end and an outlet at a second end, and a lumen extending from the inlet to the outlet so that fluid can flow therethrough;
   b. a plurality of unidirectional hook-like members on an outside of said tube so that when the stent is rotated within the urethra in one direction the members will engage the wall of the urethra and when the stent is rotated in an opposite direction the members will be disengaged from the wall of urethra.

2. A kit for anchoring a stent for maintaining fluid flow through the urethra which has a wall, said kit comprising:
   a. a tubular stent having an inlet and an outlet and a lumen through which fluid can flow, said stent having hook-like anchoring means which when the stent is rotated within the urethra will engage the wall of the urethra to prevent the stent from migrating; and
   b. an elongated grasping tool for grasping the stent in the urethra and extending outside the urethra so that the stent can be rotated in the urethra from outside the urethra to either engage or disengage the anchoring means from the wall of the urethra.

* * * * *